(12) United States Patent
Schwartz et al.

(10) Patent No.: US 8,980,876 B2
(45) Date of Patent: Mar. 17, 2015

(54) INHIBITION OF MICROBIAL GROWTH BY ACONITASE INHIBITION

(75) Inventors: James Robert Schwartz, West Chester, OH (US); Charles Winston Saunders, Fairfield, OH (US); Robert Scott Youngquist, Mason, OH (US); Jun Xu, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 268 days.

(21) Appl. No.: 13/283,894

(22) Filed: Oct. 28, 2011

(65) Prior Publication Data

US 2013/0108610 A1 May 2, 2013

Related U.S. Application Data

(60) Provisional application No. 61/407,757, filed on Oct. 28, 2010.

(51) Int. Cl.
*A01N 55/02* (2006.01)
*C07D 213/89* (2006.01)

(52) U.S. Cl.
USPC ............................................. 514/188; 546/6

(58) Field of Classification Search
USPC ............................................. 514/188; 546/6
See application file for complete search history.

(56) References Cited

U.S. PATENT DOCUMENTS

| | | | |
|---|---|---|---|
| 2,396,278 | A | 3/1946 | Otto |
| 2,438,091 | A | 3/1948 | Lynch |
| 2,486,921 | A | 11/1949 | Byerly |
| 2,486,922 | A | 11/1949 | Strain |
| 2,658,072 | A | 11/1953 | Milton |
| 2,809,971 | A | 10/1957 | Berstein |
| 3,236,733 | A | 2/1966 | Karsten |
| 3,332,880 | A | 7/1967 | Kessler |
| 3,753,196 | A | 8/1973 | Kurtz |
| 3,761,418 | A | 9/1973 | Parran |
| 3,929,678 | A | 12/1975 | Laughlin |
| 4,323,683 | A | 4/1982 | Bolich, Jr. |
| 4,345,080 | A | 8/1982 | Bolich, Jr. |
| 4,379,753 | A | 4/1983 | Bolich, Jr. |
| 4,470,982 | A | 9/1984 | Winkler |
| 5,968,539 | A | 10/1999 | Beerse |
| 6,426,093 | B1 | 7/2002 | Chevion |
| 6,846,777 | B2 | 1/2005 | Antoni-Zimmermann |
| 2006/0089342 | A1 * | 4/2006 | Gavin et al. ................... 514/184 |

FOREIGN PATENT DOCUMENTS

| | | |
|---|---|---|
| CN | 1268941 | 10/2000 |
| EP | 0158481 A2 | 10/1985 |
| EP | 0268911 A2 | 6/1988 |
| FR | 2758720 | 5/1997 |
| FR | 2758720 A1 | 8/2000 |
| FR | 2938766 A1 | 11/2008 |
| JP | 2013536864 | 9/2013 |
| WO | WO9939575 | 8/1999 |
| WO | WO9939575 | 10/1999 |
| WO | WO0100151 | 6/2000 |
| WO | WO0100151 | 1/2001 |
| WO | WO 2001072815 | 3/2001 |
| WO | WO0153495 | 7/2001 |
| WO | WO0215693 | 2/2002 |
| WO | WO2006110386 | 3/2006 |
| WO | WO2006110386 | 10/2006 |
| WO | WO 2006079565 | 1/2007 |
| WO | WO2008008537 | 1/2008 |
| WO | WO 2008134882 | 11/2008 |
| WO | WO 2007106622 | 12/2008 |
| WO | WO2008145849 | 12/2008 |
| WO | WO2009053163 | 4/2009 |
| WO | WO2008145848 | 6/2009 |
| WO | WO2008145849 | 6/2009 |
| WO | WO2011056667 | 5/2011 |

OTHER PUBLICATIONS

Zarember, K. "Antifungal Activities of Natural and Synthetic Iron Chelators Alone and in Combination with Azole and Polyene Antibiotics against *Aspergillus fumigatus*" Antimicrobial Agents and Chemotherapy, Jun. 2009, p. 2654-2656.
Kuipers, "Synergistic Fungistatic Effects of Lactoferrin in Combination with Antifungal Drugs against Clinical*Candida Isolates*" Antimicrobial Agents and Chemotherapy, Nov. 1999, p. 2635-2641.
Mabicka, A. "Synergistic wood preservatives involving EDTA, irganox 1076 and 2-hydroxypyridine-N-oxide" International Biodegradation 55 (2005) 203-211.
Ibrahim, A. "Deferiprone iron chelation as a novel therapy for experimental mucormycosis" Journal of Antimicrobial Chemotherapy (2006) 58, 1070-1073.
Ildiko, N., "Iron gathering of opportunistic pathogenic fungi" Acta Microbiologica et Immunologica Hungarica 52 (2) pp. 185-197.
Geib N, "Genome mining in Amycolatopsis balhimycina for ferredoxins capable of supporting cytochrome P450 enzymes involved in glycopeptide antibiotic biosynthesis" FEMS Microbiol Lett. May 2010;306(1):45-53. Epub Feb. 22, 2010.
Dadák V. "Electron transfer in Paracoccus denitrificans with the modified fbc operon" Folia Microbiol (Praha). Nov. 2009;54(6):475-82. Epub Feb. 7, 2010.
Hughes LM. "Probing binding determinants in center P of the cytochrome bc(1) complex using novel hydroxy-naphthoquinones" Biochim Biophys Acta. Jan. 2010;1797(1):38-43. Epub Aug. 4, 2009.
Kang Y.S. "Overexpressing antioxidant enzymes enhances naphthalene biodegradation in *Pseudomonas* sp. strain As1" Microbiology. Oct. 2007;153(Pt 10):3246-54.
Kessl JJ., "Parameters determining the relative efficacy of hydroxy-naphthoquinone inhibitors of the cytochrome bc1 complex" Biochim Biophys Acta. Apr. 2007;1767(4):319-26. Epub Feb. 27, 2007.
Tapia L.,"Effect of 13-epi-sclareol on the bacterial respiratory chain" Planta Med. Nov. 2004;70(11):1058-63.

(Continued)

*Primary Examiner* — Rosanne Kosson
(74) *Attorney, Agent, or Firm* — Linda M. Sivik

(57) ABSTRACT

The present invention is directed to a method of inhibiting aconitase activity of fungal cells in an individual, the method comprising administering an inhibitor of aconitase activity to the fungal cell in an amount effective to inhibit activity of aconitase by said fungal cells.

3 Claims, No Drawings

(56) References Cited

OTHER PUBLICATIONS

Fang J., "Rotenone-insensitive NADH dehydrogenase is a potential source of superoxide in procyclic Trypanosoma brucei mitochondria" Mol Biochem Parasitol. Aug. 28, 2002;123(2):135-42.
Gutierrez-Cirlos EB, "Inhibitory analogs of ubiquinol act anti-cooperatively on the Yeast cytochrome bc1 complex. Evidence for an alternating, half-of-the-sites mechanism of ubiquinol oxidation" J Biol Chem. Jan. 11, 2002;277(2):1195-202. Epub Nov. 7, 2001.
Nakayama Y, "Inhibitor studies of a new antibiotic, korormicin, 2-n-hepty1-4- hydroxyquinoline N-oxide and Ag+ toward the Na+-translocating NADH-quinone reductase from the marine Vibrio alginolyticus" Biol Pharm Bull. Oct. 1999;22(10):1064-7.
Ildiko, N., "Iron gathering of opportunistic pathogenic fungi" Acta Microbiologica et Immunologica Hungarica 52 (2) pp. 185-197 (2005).
Duan, X. et al. "Reactivity of nitric oxide with the [4Fe-4S] cluster of dihydroxyacid dehydratase from *Escherichia coli*" Biochem. J. (2009) 417, 783-789.
Lushchak, O.V. et al. "Sodium Nitroprusside Induces Mild Oxidative Stress in Saccharomyces Cerevisiae" Redox Report 2008, vol. 13, No. 4; 10 pages.
Morita, H. et al. "Anti-Microbial Action Against Verotoxigenic *Escherichia Coli* O157:H7 of Nitric Oxide Derived from Sodium Nitrite" Bioscience Biotechnology and Biochemistry, May 2004, vol. 68(5), p. 1027-34.
International Search Report PCT/US2011/058313; 14 pages, Jul. 29, 2013.
International Search Report PCT/US2011/058269; 13 pages, Dec. 28, 2011.
Lemesre JL, "Leishmania spp.: nitric oxide-mediated metabolic inhibition of promastigote and axenically grown amastigote forms" Exp Parasitol. May 1997;86(1):58-68.
Haraguchi H. "Mode of antibacterial action of totarol, a diterpene from Podocarpus nagi" Planta Med. Apr. 1996;62(2):122-5.
Fisher J. "Anthracycline antibiotic reduction by spinach ferredoxin-NADP+ reductase and ferredoxin." Biochemistry. Jul. 2, 1985;24(14):3562-71.
Burow, Luke C. "Anaerobic central metabolic pathways active during polyhydroxyalkanoate production in uncultured cluster 1 Defluviicoccus enriched inactivated sludge communities" FEMS MICROBIOLOGY LETTERS, Sep. 2009, vol. 298(1), p. 79-84.
Morita, H "Reactivity of nitric oxide with the [4Fe-4S] cluster of dihydroxyacid dehydratase from *Escherichia coli*" Bioscience Biotechnology and Biochemistry, May 2004, vol. 68(5), p. 1027-34.
Ke-Hung Tsui. "Zinc blocks gene expression of mitochondrial aconitase in human prostatic carcinoma cells" International Journal of Cancer, vol. 118, Issue 3, pp. 609-615, Feb. 1, 2006.
Zigiang Yu, "Zinc inhibits mitochondrial aconitase expression in prostate cancer cells" Cellular and Molecular Biology 4: Gene Expression I, Proc Amer Assoc Cancer Res, vol. 47, 2006.
Lushchak, O.V. et al. "Sodium Nitroprusside Induces Mild Oxidative Stress in *Saccharomyces Cerevisiae*".
Bharadwaj, A. An Invitro Study to Evaluate the Synergisitc Activity of Norfloxacin and Metronidazole, R. Bharadwaj, et al., *Indian J Pharmacol* 2003, 35: 220-226.
International Search Report PCT/US2011/058313; 14 pages.
International Search Report PCT/US2011/058269; 13 pages.
USPTO Office Action for U.S. Appl. No. 13/283,890 dated Jun. 17, 2013.
USPTO Office Action for U.S. Appl. No. 13/283,890 dated Oct. 13, 2013.
Duan, X. "Reactivity of nitric oxide with the [4Fe-4S] cluster of dihydroxyacid dehydratase from *Escherichia coli*" Biochem. J. 2009, 417, p. 783-789.

\* cited by examiner

INHIBITION OF MICROBIAL GROWTH BY ACONITASE INHIBITION

FIELD OF THE INVENTION

The present invention is directed to a method of inhibiting aconitase activity of fungal cells in an individual, the method comprising administering an inhibitor of aconitase activity to the fungal cell in an amount effective to inhibit activity of aconitase by said fungal cells.

BACKGROUND OF THE INVENTION

Without being bound by theory, it is believed that the anti-fungal mechanism of action of pyrithione-containing antifungals involves the inhibition of aconitase and other mitochondrial iron-sulfur proteins. The mechanism of inhibition is believed to involve the formation of copper pyrithione within the cell by either association with exogenous or endogenous copper and transchelation according to the Irving-Williams series. The copper pyrithione can then traverse the mitochondrial membrane and interact with iron-sulfur proteins such as aconitase resulting in alteration of the iron-sulfur active site and resultant inhibition of activity.

In the present invention it was found that the ZPT sensitivity increased with a CUP2 deletion strain that is defective in protection from high copper levels. From this and other observations, it is appreciated that copper is augmenting the effect of ZPT induced growth inhibition, but the mechanism was unknown.

Through the present invention, including the results of ZPT sensitivity of the Saccharomyces deletion library strains, it is found that mitochondrial iron sulfur protein maturation is a key target of ZPT. This is confirmed by the present invention's demonstration that, in minimal medium, ZPT inhibits growth by inhibition of glutamate and lysine synthesis, which require the activity of the mitochondrial iron-sulfur protein aconitase. Moreover, culturing of cells in the presence of ZPT has led to aconitase inhibition. The present invention has extended the understanding of the ZPT mechanism of action to identification of a key target enzyme.

SUMMARY OF THE INVENTION

A method of inhibiting aconitase activity of fungal cells in an individual, the method comprising administering an inhibitor of aconitase to the fungal cell in an amount effective to inhibit the activity of aconitase by said fungal cell.

DETAILED DESCRIPTION OF THE INVENTION

While the specification concludes with claims which particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

Herein, "aconitase inhibition" means a reduction in aconitase activity that can be recovered from lysed cells. Such aconitase inhibition may include direct inhibition of the enzyme or prevention of synthesis of active aconitase. Synthesis of active aconitase may be due to the lack of synthesis of aconitase protein, the lack of proper folding of the aconitase protein, the lack of incorporation of a functional iron-sulfur cluster into aconitase, or the presence of a damaged iron-sulfur cluster in aconitase.

Herein, "personal care composition" means products for and/or methods relating to treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); and shaving.

A. Pyrithione or a Polyvalent Metal Salt of Pyrithione

In an embodiment, the present invention may comprise pyrithione or a polyvalent metal salt of pyrithione. Any form of polyvalent metal pyrithione salts may be used, including platelet and needle structures. In a further embodiment, salts for use herein include those formed from the polyvalent metals magnesium, barium, bismuth, strontium, copper, zinc, cadmium, zirconium and mixtures thereof, and in further embodiment, zinc. In yet a further embodiment, for use herein is the zinc salt of 1-hydroxy-2-pyridinethione (known as "zinc pyrithione" or "ZPT"); in another embodiment, ZPT in platelet particle form, wherein the particles have an average size of up to about 20 µm, and in an embodiment have an average size of up to about 5 µm, and yet in a further embodiment have an average size of up to about 2.5 µm.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

It is further contemplated that when ZPT is used as the anti-microbial particulate in the anti-microbial compositions herein, that an additional benefit of hair growth or re-growth may be stimulated or regulated, or both, or that hair loss may be reduced or inhibited, or that hair may appear thicker or fuller.

Zinc pyrithione may be made by reacting 1-hydroxy-2-pyridinethione (i.e., pyrithione acid) or a soluble salt thereof with a zinc salt (e.g. zinc sulfate) to form a zinc pyrithione precipitate, as illustrated in U.S. Pat. No. 2,809,971.

An embodiment of the present invention includes from about 0.01% to about 5% of a pyrithione or polyvalent metal salt of a pyrithione; and in a further embodiment from about 0.1% to about 2%.

Method

Cultures of *Saccharomyces cerevisiae* strain BY4741 are grown in YPD (20 grams glucose, 20 grams peptone, 10 grams yeast extract per liter) broth overnight at 30°. The cultures are diluted with YPD to a total volume of 100 mls with an optical density (600 nm) of 0.1. The cultures are incubated with shaking until reaching an optical density of 0.2, whereupon the test material is added. The cultures are incubated overnight, and the cells are pelleted by centrifugation. The cell pellet is washed with 100 mM NaCl, 20 mM Tris pH 7.4 and resuspended in 5 ml of 100 mM NaCl, 20 mM Tris pH 7.4. Glass beads (0.5 mm) is added. The sample is alternately vortexed for one minute and incubated on ice for one minute, with a total of ten treatments. After centrifugation, the supernatant is collected. In a 96-well plate (UV-transparent Corning 3679 plate), 30 µl of cell lysate is mixed with 20 µl 100 mM NaCl, 20 mM Tris pH 7.4 and assayed using a Bioxytech Aconitase-340 kit (OxisResearch) according to instructions.

For the aconitase assay, samples are incubated for six minutes at 37°. The reaction rate is calculated based on the increase in optical density (340 nm) in the five-minute interval beginning one minute after the reaction started. The aconitase activity in lysates of treated samples is divided by the aconitase activity in lysates of untreated samples. If replicates were performed on samples, the reported data are a mean of the aconitase activity measurements of individual lysates of treated cells divided by the mean of the aconitase activity measurements of individual lysates of untreated cells. If the aconitase activity appears to be negative in lysates of treated cells, the value "0" is reported for aconitase activity (Table 1).

TABLE 1

| Material | Concentration, ppm | Aconitase Activity, % of Untreated Control |
|---|---|---|
| Zinc pyrithione (ZPT) | 5 | 0 |
| Copper Pyrithione (CuPT) | 5 | 0 |
| 1,10-Phenanthroline | 50 | 2 |
| N-Hydroxy-6-octyloxypyridine-2(1H)one, ethanolamine salt (1) | 50 | 0 |
| Piroctone Diamine (Octopirox) | 50 | 0 |
| 8-Hydroxyquinoline | 50 | 15 |
| EDTA | 50 | 36 |
| Zinc Sulfate | 50 | 110 |

(1) From Arch Chemicals, Inc.

Desirable materials inhibit aconitase activity under the specified conditions by 70% or more (meaning in Table 1 residual activities of 30% or less). As demonstrated, both zinc and copper pyrithiones have the expected inhibition, as expected from the proposed mechanism of action. Other materials exemplified in Table 1 have affinity for metal ions as well, potentially influencing the iron-sulfur protein active site in a similar manner to the pyrithiones. For comparison, certain classical chelators, such as EDTA, are not effective, presumably due to poor cellular membrane permeation.

Aconitase inhibition has not previously been appreciated as a target for control of fungi. Thus, aconitase inhibitors such as the following list, while not intended to be limiting, are included as anti-fungal;

Fluorocitrate—from fluoroacetate
nitroisocitrate
4-hydroxy-trans-aconitate
oxalomalate (OMA, alpha-hydroxy-beta-oxalosuccinic acid)
ROS Species or Oxidizing Species
   Peroxynitrite
   Nitric Oxide
   Hydrogen peroxide
   superoxide
Organic Molecules from One Paper
   1,2,3-D,L-Tricarboxycyclopentene-1
   Trimesic acid (1,3,5-tricarboxybenzene)
   Trimellitic acid (1,2,4-tricarboxybenzene)
   Pyromellitic acid (1,2,4,5-tetracarboxybenzene)
   1,2,3,4-Tetracarboxycyclopentane
Kreb Cycle Materials
   oxalosuccinate
   trans-aconitate
   cis-aconitate
   alpha-ketoglutaric
   2-oxoglutarate
   oxaloacetate
Others
   alloxan
   1-methyl-4-phenylpyridine
   Manganese
   Lon protease
   Deferiprone
   Pyrithione or metal salts of pyrithione
   Zinc pyrithione
   N-Hydroxy-6-octyloxypyridine-2(1H)one, ethanolamine salt, (HP-101) as supplied from Arch Chemicals, Inc., is part of the N-Hydroxypyridones. The N-Hydroxypyridones have alkyl ether substitutions at the 6-position as free acids, ethanolamine salts and metal salts such as zinc, N-Hydroxy-6-octyloxypyridine-2(1H)one, zinc salt. The alkyl ether substituent is from 2-22 carbons in length, either linear or branched.

In an embodiment of the present invention, further iron-sulfur enzymes may be useful targets in a similar manner as is aconitase. Non-limiting examples of such enzymes include biotin synthase, lipoic acid synthase, and homoaconitase.

In the present invention, an aconitase inhibitor may be used alone, or in combination with additional aconitase inhibitors and mixtures thereof. For example, zinc pyrithione may be used in combination with one or more additional aconitase inhibitors.

In an embodiment of the present invention, the present invention comprises a method of inhibiting aconitase activity of fungal cells or microbial cells, the method comprising administering an inhibitor of aconitase activity, or an aconitase inhibitor to the fungal or microbial cell in an individual in an amount effective to inhibit activity of aconitase by said fungal cells.

In an embodiment of the present invention, the present invention comprises a method of inhibiting aconitase activity of fungal cells or microbial cells, in an individual, the method comprising administering an inhibitor of aconitase activity, or an aconitase inhibitor to the fungal or microbial cell in an individual in an amount effective to inhibit activity of aconitase by said fungal cells.

In a further embodiment, the present invention comprises a method of inhibiting aconitase activity of fungal cells wherein the individual is a dandruff sufferer.

In yet a further embodiment, the present invention comprises a method of inhibiting aconitase activity of fungal cells wherein the inhibitor of aconitase is selected from the group consisting of fluorocitrate, 4-hydroxy-trans-aconitate, oxalomalate, alpha-hydroxy-beta-oxalosuccinic acid), ROS species or oxidizing Species, peroxynitrite, nitric oxide, hydrogen peroxide, superoxide, 1,2,3-D,L-tricarboxycyclopentene-1, trimeric acid (1,3,5-tricarboxybenzene), trimellitic acid (1,2,4-tricarboxybenzene), pyromellitic acid (1,2,4,5-tetracarboxybenzene), 1,2,3,4-tetracarboxycyclopentane, kreb cycle materials, oxalosuccinate, trans-aconitate, cis-aconitate, alpha-ketoglutaric, 2-oxoglutarate, oxaloacetate, alloxan, 1-methyl-4-phenylpyridine, manganese, Lon protease, N-Hydroxy-6-octyloxypyridine-2(1H)one, ethanolamine salt pyrithione and metal salts of pyrithione, zinc pyrithione and mixtures thereof.

In a further embodiment, the present invention comprises a method of inhibiting aconitase activity of fungal wherein the inhibitor of aconistase activity is zinc pyrithione.

In an embodiment, the present invention comprises a method of inhibiting aconitase activity of fungal cells wherein the inhibitor of aconitase inhibits aconitase activity by at least 70%.

In a further embodiment, the present invention comprises a method of inhibiting aconitase activity for an antifungal benefit comprising the steps of: a) exposing a cell to a material; b) opening of cell and measuring an aconitase activity and c) measuring the reduction in aconitase activity compared to a baseline or a control/untreated sample.

In a yet another embodiment, the present invention discloses a method of inhibiting the growth of a fungal cell, said method comprising contacting said fungal cell with a material which inhibits aconitase activity by at least 70%, thereby causing an inhibition of growth of said fungal cell and/or causing death of the cell.

In a further embodiment, the present invention discloses a personal care composition comprising one or more of a material having inhibitory activity against an aconitase enzyme, wherein the material inhibits aconitase activity, by at least 70%, to provide enhanced efficacy to treat anti-fungal mediated conditions, such as anti-fungal mediated scalp conditions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting aconitase activity of fungal cells in an individual, the method comprising administering a composition comprising an inhibitor of aconitase activity to the fungal cell in an amount effective to inhibit activity of aconitase by said fungal cells wherein the inhibitor of aconitase activity is zinc pyrithione or another metal salt of pyrithione and wherein the inhibitor of aconitase inhibits aconitase activity by at least 70%.

2. A method of inhibiting aconitase activity of fungal cells according to claim 1 wherein the individual is a dandruff sufferer.

3. A method of inhibiting the growth of fungal cells in a material, the method comprising contacting the material with a composition comprising an inhibitor of aconitase activity in an amount effective to inhibit the activity of aconitase by said fungal cells, wherein the inhibitor of aconitase activity is zinc pyrithione or another metal salt of pyrithione, and wherein the inhibitor of aconitase inhibits the aconitase activity by at least 70%.

* * * * *